United States Patent
Jeong et al.

(10) Patent No.: US 10,538,529 B2
(45) Date of Patent: Jan. 21, 2020

(54) POLYMORPHIC FORMS OF TRIAZOLOPYRAZINE DERIVATIVES AND METHOD OF PREPARING THE SAME

(71) Applicant: ABION Inc, Seoul (KR)

(72) Inventors: Seong-Hoon Jeong, Goyang (KR); Ki-Hyun Kim, Goyang (KR); Nam-Ah Kim, Incheon (KR)

(73) Assignee: ABION Inc, Seoul (KR)

( * ) Notice: Subject to any disclaimer, the term of this patent is extended or adjusted under 35 U.S.C. 154(b) by 0 days.

(21) Appl. No.: 16/308,457

(22) PCT Filed: Jan. 24, 2018

(86) PCT No.: PCT/KR2018/001038
§ 371 (c)(1),
(2) Date: Dec. 8, 2018

(87) PCT Pub. No.: WO2018/147575
PCT Pub. Date: Aug. 16, 2018

(65) Prior Publication Data
US 2019/0270747 A1    Sep. 5, 2019

(30) Foreign Application Priority Data
Feb. 8, 2017 (KR) .................. 10-2017-0017440

(51) Int. Cl.
*C07D 487/04* (2006.01)

(52) U.S. Cl.
CPC ........ *C07D 487/04* (2013.01); *C07B 2200/13* (2013.01)

(58) Field of Classification Search
CPC .................................................. C07D 487/004
See application file for complete search history.

(56) References Cited

U.S. PATENT DOCUMENTS

| 7,732,604 | B2 | 6/2010 | Cheng et al. |
| 8,435,986 | B2 | 5/2013 | Stieber et al. |
| 8,507,487 | B2 | 8/2013 | Su et al. |
| 8,586,599 | B2 | 11/2013 | Becker et al. |
| 9,403,831 | B2 | 8/2016 | Jung et al. |

FOREIGN PATENT DOCUMENTS

| KR | 2011-0051243 A | 5/2011 |
| KR | 2012-0125261 A | 11/2012 |
| KR | 2011-0089462 A | 10/2016 |
| KR | 2014-0022229 A | 6/2017 |
| WO | 2015-046653 A1 | 4/2015 |

OTHER PUBLICATIONS

International Search Report for PCT/KR2018/001038 dated May 24, 2018.

*Primary Examiner* — Paul V Ward

(57) ABSTRACT

A crystalline modification of triazolopyrazine derivatives binds to a hepatocyte growth factor (HGF) to activate phosphorylation, thereby significantly inhibiting the activity of c-Met kinase triggering cell proliferation, migration, and formation of new blood vessels. Therefore, the compound of the present application may be effectively used for the treatment or prevention of various hyper proliferative disorders mediated by hyper proliferation activation of cells and excessive angiogenesis.

30 Claims, 14 Drawing Sheets

POLYMORPHIC FORMS OF TRIAZOLOPYRAZINE DERIVATIVES AND METHOD OF PREPARING THE SAME

CROSS REFERENCE TO RELATED APPLICATIONS

This application claims priority to Korean Patent Application No. 10-2017-0017440, filed on Feb. 8, 2017. Further, the application is the National Phase application of International Application No. PCT/KR2018/001038, filed on Jan. 24, 2018, which designates the United States. Each of these applications is hereby incorporated by reference in their entirety into the present application.

TECHNICAL FIELD

The present application relates to crystalline modifications of triazolopyrazine derivatives and a method of preparing the same.

BACKGROUND ART

The compound of the following Chemical Formula 1 is first disclosed in Korean Patent Publication No. 10-2014-0022229 filled on Aug. 13, 2012. The compound of Chemical Formula 1 is described as Chemical Formula 17 in the Patent Document, but crystalline modifications of the compound of Chemical Formula 1 are not described.

Specific crystalline substances, i.e., structures or polymorphic forms of a pharmaceutical compound may be objects of interest to those involved in the development of suitable dosage forms. This is because the precise dosage used or measured for one type of structure or form may not be applicable to another type of structure or form when a specific crystalline or polymorphic form is not maintained consistent during clinical and stability studies.

Once a pharmaceutical compound has been prepared for use, it is important to identify the structures or polymorphic forms that are carried in each dosage form to maintain the same form in manufacturing process and ensure that the same amount of drug is contained in each dosage. Thus, it is desired to ensure that there is a consistent structure or polymorphic forms, or a consistent combination of structures or polymorphic forms. In addition, characteristic structures or polymorph forms may exhibit enhanced thermodynamic stability and may be more suitable than other structures or polymorphs to be included in pharmaceutical formulations.

In the present application, reference to any literature does not constitute admission to prior art related to the present application.

PRIOR ART DOCUMENTS

Patent Documents (Patent Document 1) KR2014-0022229A
(Patent Document 2) KR2011-0111472A
(Patent Document 3) U.S. Pat. No. 8,507,487B2

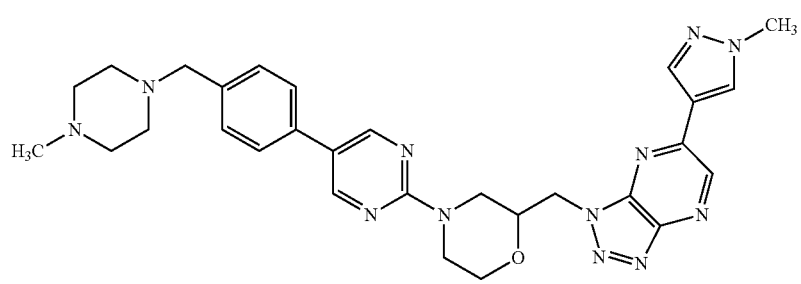

[Chemical Formula 1]

DISCLOSURE

Technical Problems

An object of the present application is to provide crystalline modifications of triazolopyrazine derivatives and a method of manufacturing the same.

Technical Solutions

The present application provides crystalline modifications of the compound of the following Chemical Formula 1 and a method of manufacturing the same.

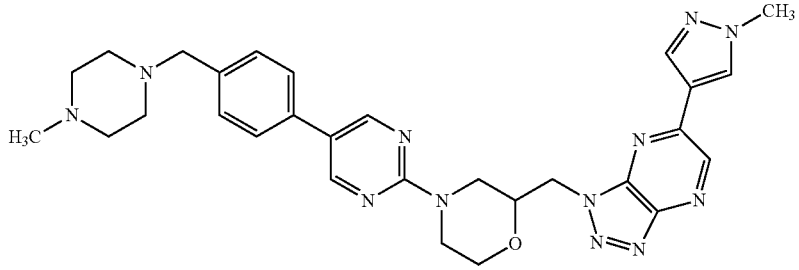

[Chemical Formula 1]

The present inventors have made many efforts to develop compositions for preventing or treating efficiently various hyper proliferative disorders caused by the activity of abnormal tyrosine kinases by finding compounds having an inhibitory activity against tyrosine kinase. As a result, it has been found that crystalline modifications of the compound of Chemical Formula 1 which are not known up to now significantly inhibit the activity of c-Met kinase.

According to exemplary embodiments of the present invention, the crystalline modification of the compound of Chemical Formula 1 binds to a hepatocyte growth factor (HGF) to activate phosphorylation, thereby significantly inhibiting the activity of c-Met kinase triggering cell proliferation, migration, and formation of new blood vessels. Therefore, the compound of the present disclosure may be effectively used for the treatment or prevention of various hyper proliferative disorders mediated by hyper proliferation activation of cells and excessive angiogenesis.

In addition, the preparation of the crystalline modification of the compound of Chemical Formula 1 may be used to increase the purity of the finally obtained form. The crystalline modification of the compound of Chemical Formula 1 may exhibit different physical characteristics, for example, melting point, hygroscopicity, solubility, fluidity, or thermal stability. Accordingly, the crystalline modification of the compound of Chemical Formula 1 may be used to select the most suitable form for given uses or aspects, for example, separate administration forms in a drug manufacturing process, such as tablets, capsules, ointments, suspensions, or solutions, or intermediates in preparation of drug forms with optimal pharmacokinetic properties.

XRD peaks of a crystalline modification type I compound of Chemical Formula 1 may include, for example, 3.35°, 6.75°, 7.94°, 10.40° and 12.37° (°2θ, ±0.1° using Cu-Kα1 radiation). As another embodiment, XRD peaks of the crystalline modification type I compound of Chemical Formula 1 may include 13.86°, 15.96°, 18.78°, and 19.89° (°2θ, ±0.1° using Cu-Kα1 radiation). In addition, in one example, XRD peaks of the crystalline modification I type compound of Chemical Formula 1 may include 20.59°, 21.01°, 24.82°, and 28.46° (°2θ, ±0.1° using Cu-Kα1 radiation). In one embodiment, XRD peaks of the crystalline modification type I compound of Chemical Formula 1 may include preferably 3.35°, 6.75°, 7.94°, 10.40°, 12.37°, 13.86°, 15.96°, 18.78°, 19.89°, 20.59°, 21.01°, 24.82°, and 28.46° (°2θ, ±0.1° using Cu-Kα1 radiation).

XRD peaks of a crystalline modification type II compound of Chemical Formula 1 may include, for example, 5.81°, 7.10°, 8.49°, 9.32°, 11.74°, 15.97°, and 16.45° (°2θ, ±0.1° using Cu-Kα1 radiation). As another embodiment, XRD peaks of the crystalline modification type II compound of Chemical Formula 1 may include 16.85°, 17.95°, 19.59°, 19.93°, 20.91°, 22.63°, and 24.50° (°2θ, ±0.1° using Cu-Kα1 radiation). In addition, in one example, XRD peaks of the crystalline modification type II compound of Chemical Formula 1 may include 26.86°, 29.62°, 30.95°, 32.51°, and 37.15° (°2θ, ±0.1° using Cu-Kα1 radiation). In one embodiment, XRD peaks of the crystalline modification type II compound of Chemical Formula 1 may include preferably 5.81°, 7.10°, 8.49°, 9.32°, 11.74°, 15.97°, 16.45°, 16.85°, 17.95°, 19.59°, 19.93°, 20.91°, 22.63°, 24.50°, 26.86°, 29.62°, 30.95°, 32.51°, and 37.15° (°2θ, ±0.1° using Cu-Kα1 radiation).

XRD peaks of a crystalline modification type III compound of Chemical Formula 1 may include, for example, 3.01°, 6.81°, 7.33°, and 12.28° (°2θ, ±0.1° using Cu-Kα1 radiation). As another embodiment, XRD peaks of the crystalline modification type III compound of Chemical Formula 1 may include 13.44°, 13.77°, 16.03°, and 20.59° (°2θ, ±0.1° using Cu-Kα1 radiation). In addition, in one example, XRD peaks of the crystalline modification type III compound of Chemical Formula 1 may include 23.99°, 30.71°, and 33.58° (°2θ, ±0.1° using Cu-Kα1 radiation). In one embodiment, XRD peaks of the crystalline modification type III compound of Chemical Formula 1 may include preferably 3.01°, 6.81°, 7.33°, 12.28°, 13.44°, 13.77°, 16.03°, 20.59°, 23.99°, 30.71°, and 33.58° (°2θ, ±0.1° using Cu-Kα1 radiation).

XRD peaks of a crystalline modification type IV compound of Chemical Formula 1 may include, for example, 5.81°, 6.93°, 8.42°, 9.43°, and 11.53° (°2θ, ±0.1° using Cu-Kα1 radiation). As another embodiment, XRD peaks of the crystalline modification type IV compound of Chemical Formula 1 may include 14.84°, 16.33°, 16.89°, 17.79°, and 19.92° (°2θ, ±0.1° using Cu-Kα1 radiation). In addition, in one example, XRD peaks of the crystalline modification type IV compound of Chemical Formula 1 may include 24.20°, 26.88°, 27.41°, 28.85°, and 32.04° (°2θ, ±0.1° using Cu-Kα1 radiation). In one embodiment, XRD peaks of the crystalline modification type IV compound of Chemical Formula 1 may include preferably 5.81°, 6.93°, 8.42°, 9.43°, 11.53°, 14.84°, 16.33°, 16.89°, 17.79°, 19.92°, 24.20°, 26.88°, 27.41°, 28.85°, and 32.04° (°2θ, ±0.1° using Cu-Kα1 radiation).

XRD peaks of a crystalline modification type V compound of Chemical Formula 1 may include, for example, 8.71°, 9.67°, 11.36°, and 11.66° (°2θ, ±0.1° using Cu-Kα1 radiation). As another embodiment, XRD peaks of the crystalline modification type V compound of Chemical Formula 1 may include 13.44°, 16.23°, 18.80°, and 21.09° (°2θ, ±0.1° using Cu-Kα1 radiation). In addition, in one example, XRD peaks of the crystalline modification type V compound of Chemical Formula 1 may include 21.44°, 23.55°, and 23.96° (°2θ, ±0.1° using Cu-Kα1 radiation). In one embodiment, XRD peaks of the crystalline modification type V compound of Chemical Formula 1 may include preferably 8.71°, 9.67°, 11.36°, 11.66°, 13.44°, 16.23°, 18.80°, 21.09°, 21.44°, 23.55°, and 23.96° (°2θ, ±0.1° using Cu-Kα1 radiation).

XRD peaks of a crystalline modification type VI compound of Chemical Formula 1 may include, for example, 3.40°, 6.96°, 7.50°, 9.68°, and 12.50° (°2θ, ±0.1° using Cu-Kα1 radiation). As another embodiment, XRD peaks of the crystalline modification type VI compound of Chemical Formula 1 may include 13.46°, 13.98°, 15.65°, 17.70°, and 21.05° (°2θ, ±0.1° using Cu-Kα1 radiation). In addition, in one example, XRD peaks of the crystalline modification type VI compound of Chemical Formula 1 may include 24.60°, 30.46°, 32.45°, and 33.04° (°2θ, ±0.1° using Cu-Kα1 radiation). In one embodiment, XRD peaks of the crystalline modification type VI compound of Chemical Formula 1 may include preferably 3.40°, 6.96°, 7.50°, 9.68°, 12.50°, 13.46°, 13.98°, 15.65°, 17.70°, 21.05°, 24.60°, 30.46°, 32.45°, and 33.04° (°2θ, ±0.1° using Cu-Kα1 radiation).

XRD peaks of a crystalline modification type VII compound of Chemical Formula 1 may include, for example, 3.09°, 6.31°, and 6.78° (°2θ, ±0.1° using Cu-Kα1 radiation). As another embodiment, XRD peaks of the crystalline modification type VII compound of Chemical Formula 1 may include 7.30°, 9.54°, and 11.67° (°2θ, ±0.1° using Cu-Kα1 radiation). In addition, in one example, XRD peaks of the crystalline modification type VII compound of Chemical Formula 1 may include 13.04°, 14.84°, and 24.00°

(°2θ, ±0.1° using Cu-Kα1 radiation). In one embodiment, XRD peaks of the crystalline modification type VII compound of Chemical Formula 1 may include preferably 3.09°, 6.31°, 6.78°, 7.30°, 9.54°, 11.67°, 13.04°, 14.84°, and 24.00° (°2θ, ±0.1° using Cu-Kα1 radiation).

According to another aspect of the present application, there is provided a pharmaceutical composition containing a therapeutically effective amount of a crystalline modification of the compound of Chemical Formula 1. For example, exemplary embodiments of the present invention provide a pharmaceutical composition for prevention or treatment of hyper proliferative disorders containing the crystalline modification of the compound of Chemical Formula 1 as an active ingredient.

In this specification, the term "hyper proliferative disorder" refers to a pathological state caused by excessive growth, division, and migration of cells that are not normally regulated by a general restriction means in an animal which normally growing. Examples of the hyper proliferative disorders prevented or treated with the composition of the present invention include cancer, diabetic retinopathy, retinopathy of prematurity, corneal transplant rejection, neovascular glaucoma, hypoxia, proliferative retinopathy, psoriasis, rheumatoid arthritis, osteoarthritis, autoimmune disease, Crohn's disease, recurrent stenosis, atherosclerosis, intestinal adhesions, ulcers, hepatopathy, glomerulonephritis, diabetic nephropathy, malignant neuropathy, thrombotic microangiopathy, organ graft rejection, and glomerulopathy, but are not limited thereto and include all hyper proliferative disorders which are caused by abnormal proliferation of cells and overgrowth of new blood vessels.

Further, the cancer which is one of the hyper proliferative disorders which can be prevented and treated with the composition of the present disclosure includes lung cancer, gastric cancer, pancreatic cancer, colon cancer, ovarian cancer, renal cell cancer, prostate cancer or brain tumor.

When the composition of the present application is prepared from a pharmaceutical composition, the pharmaceutical composition of the present disclosure includes a pharmaceutically acceptable carrier. The pharmaceutically acceptable carriers to be contained in the pharmaceutical composition of the present disclosure are carriers generally used in preparation and include lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate and mineral oil, but are not limited thereto. The pharmaceutical composition of the present disclosure may further include a lubricant, a wetting agent, a sweetening agent, a flavoring agent, an emulsifying agent, a suspending agent, a preservative, and the like in addition to the above ingredients.

The present application also relates to a method for preparing a crystalline modification of the compound of Chemical Formula 1.

In one embodiment of the preparation method of the present application, a method of preparing a crystalline modification type I of the compound of Chemical Formula 1 includes:

(a) stirring 30 to 70 mg of the compound of Chemical Formula 1 in a solvent mixture consisting of 30 to 70 mL of ethanol (EtOH) and 1 to 3 mL of ethyl acetate (EA);

(b) stirring the dispersion produced in step (a) at 55 to 95° C. for 30 to 60 minutes and cooling the dispersion to 5 to 45° C. in an ice water bath; and (c) recovering a material precipitated in step (b) by filtration, subsequently washing the precipitated material with distilled water, and drying the washed material under reduced pressure at 20 to 45° C.

In another embodiment of the present application, a method of preparing a crystalline modification type II of the compound of Chemical Formula 1 includes:

(a) dissolving or dispersing 30 to 70 mg of a crystalline modification type I compound of Chemical Formula 1 in 0.5 to 2 mL of methanol;

(b) stirring the dispersion produced in step (a) at 15 to 28° C. for 1 to 24 hours; and (c) recovering a material precipitated in step (b) by filtration, subsequently washing the precipitated material with distilled water, and drying the washed material under reduced pressure at 20 to 45° C. for 24 hours.

In yet another embodiment of the present application, a method of preparing a crystalline modification type III of the compound of Chemical Formula 1 includes:

(a) dissolving 30 to 70 mg of a crystalline modification type I compound of Chemical Formula 1 in 0.5 to 2 mL of tetrahydrofuran (THF);

(b) stirring the dispersion produced in step (a) at 15 to 28° C. for 1 to 24 hours; and (c) recovering a material precipitated in step (b) by filtration, subsequently washing the precipitated material with distilled water, and evaporating and drying the washed material under reduced pressure at 20 to 60° C. for 24 hours.

In still another embodiment of the present application, a method of preparing a crystalline modification type IV of the compound of Chemical Formula 1 includes:

(a) dissolving or dispersing 30 to 70 mg of a crystalline modification type I compound of Chemical Formula 1 in 0.5 to 1 mL of dichloromethane;

(b) stirring the dispersion produced in step (a) at 15 to 28° C. for 1 to 24 hours;

(c) adding 1 to 5 mL of acetonitrile (ACN) to the solution of step (b) and refrigerating the mixture for 4 hours; and (d) filtering the compound produced in step (c) and then drying the filtered compound at 15 to 28° C. for 24 hours.

In still yet another embodiment of the present application, a method of preparing a crystalline modification type V of the compound of Chemical Formula 1 includes:

(a) dissolving 30 to 70 mg of a crystalline modification type I compound of Chemical Formula 1 in 0.5 to 1 mL of dimethylsulfoxide (DMSO);

(b) stirring the dispersion produced in step (a) at 15 to 28° C. for 1 to 24 hours; and (c) filtering a material precipitated in step (b), completely evaporating the solvent dimethylsulfoxide (DMSO), and then drying the evaporated mixture.

In still yet another embodiment of the present application, a method of preparing a crystalline modification type VI of the compound of Chemical Formula 1 includes:

(a) dissolving or dispersing 30 to 70 mg of a crystalline modification type I compound of Chemical Formula 1 in 0.2 to 1 mL of dichloromethane;

(b) stirring the dispersion produced in step (a) at 15 to 28° C. for 1 to 24 hours; and (c) recovering a material precipitated in step (b) by filtration, adding 1 to 4 mL of methanol, and then subsequently washing the produced crystals with distilled water, and drying the produced crystals at 15 to 28° C.

In still yet another embodiment of the present application, a method of preparing a crystalline modification type VII of the compound of Chemical Formula 1 includes:

(a) dissolving or dispersing 30 to 70 mg of a crystalline modification type I compound of Chemical Formula 1 in 0.5 to 2 mL of water;

(b) stirring a dispersion produced in step (a) at 15 to 28° C. for 1 to 24 hours; and (c) recovering a material precipitated in step (b) by filtration and drying the recovered material at 15 to 28° C.

In the method of preparing the crystalline modifications of the Chemical Formula 1 of the present application, the filtering step and the drying step may be performed by general methods, and are not particularly limited. In addition, in this specification, the term "room temperature" means an indoor temperature, for example, a temperature of 15 to 28° C.

Advantageous Effects

The present application relates to crystalline modification compounds of triazolo pyrazine derivatives and a method of preparing the same, and the compounds may be usefully used as therapeutic agents of various hyper proliferative disorders, such as cancer, psoriasis, rheumatoid arthritis, diabetic retinopathy, and the like, related with excessive proliferation and growth of cells caused by abnormal activity of kinase by effectively inhibiting the activity of c-Met tyrosine kinase. Further, the present application provides a pharmaceutical composition for inhibiting activity of c-Met tyrosine kinase containing the crystalline modification compounds as an active ingredient and a pharmaceutical composition for preventing or treating hyper proliferative disorders.

EXEMPLARY MODES

Hereinafter, the present application will be described in detail through Examples according to the present application, but the scope of the present application is not limited by the following Examples.

The present application relates to the crystalline modification of the compound of Chemical Formula 1 capable of effectively preventing or treating various hyper proliferative disorders by inhibiting the activity of c-Met kinase and a method of preparing the same. The compound represented by Chemical Formula 1 was prepared by a method proposed in Korean Patent Publication No. KR 10-2014-0022229, and the present disclosure relates to a novel crystalline form of the compound represented by Chemical Formula 1 and hereinafter, a method of crystallizing the compound represented by Chemical Formula 1 will be described.

Hereinafter, Examples to be described below may be modified into various other forms, and the scope of the present invention is not limited to Examples to be described below. Examples of the present invention are provided to those skilled in the art for more completely describing the present invention.

Figure 1:
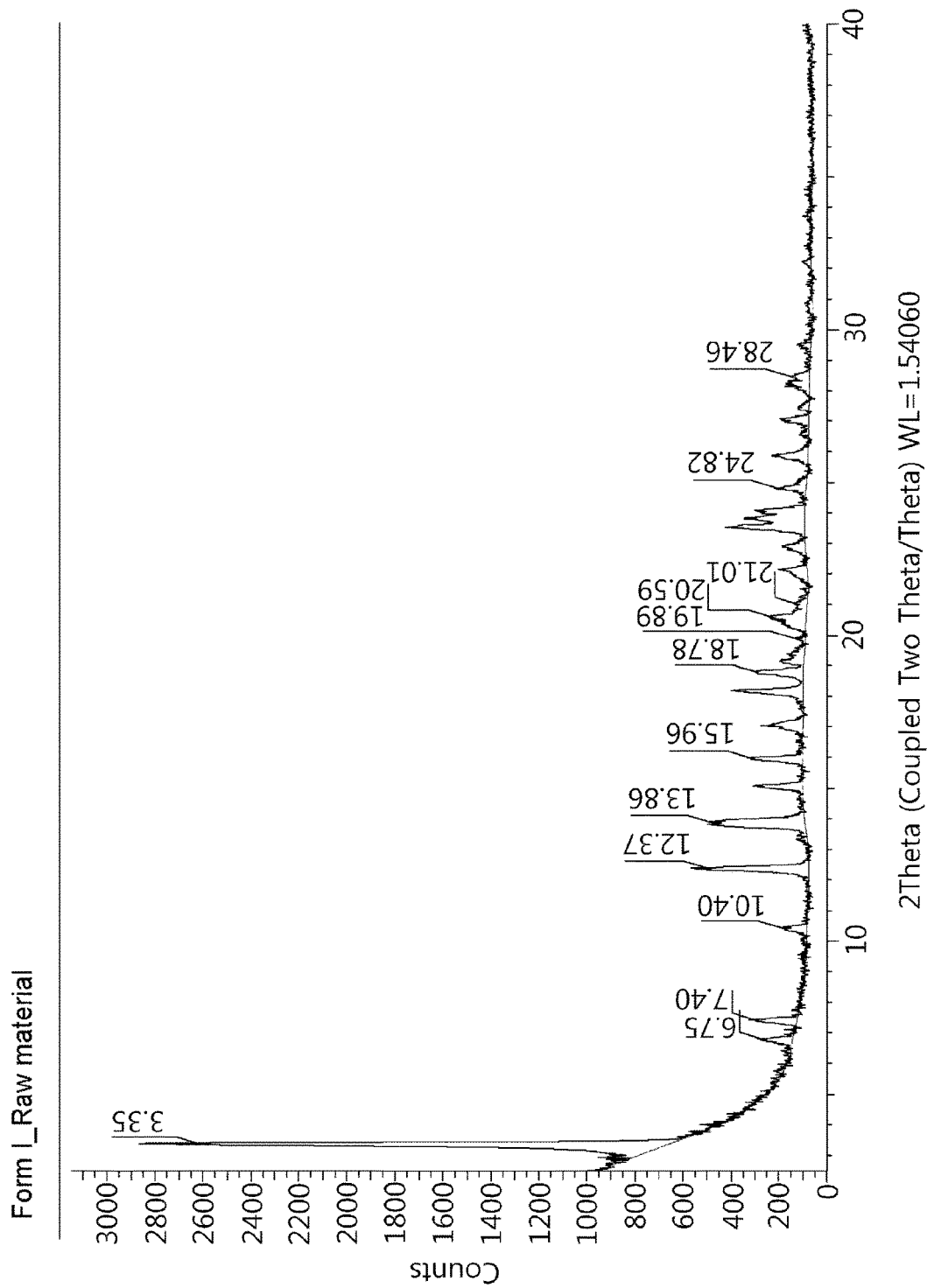
FIG. 1 shows a powder X-ray diffractogram of a crystalline modification type I compound of Chemical Formula 1 of the present disclosure.
Figure 2:
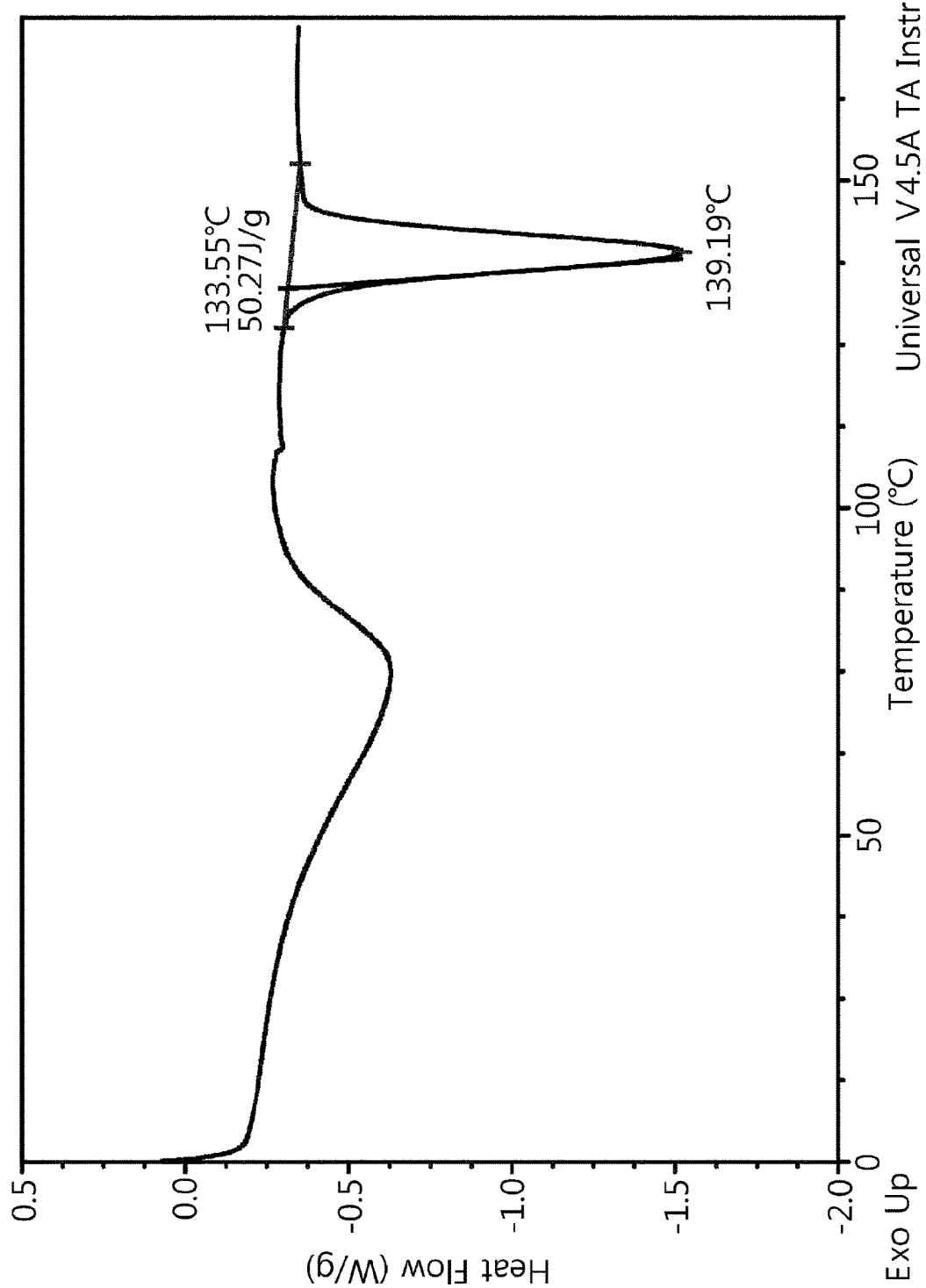
FIG. 2 shows a heat flow of the crystalline modification type I compound of Chemical Formula 1 of the present disclosure.

Example 1: Preparation of Crystalline Modification Type I Compound 50 mg of the compound of Chemical Formula 1 was stirred at 75° C. for 1 hour in a solvent mixture containing 50 mL of ethanol (EtOH) and 1 mL of ethyl acetate (EA). The dispersion was cooled to 25° C. in an ice water bath and filtered, and the produced crystals were dried under reduced pressure at room temperature. Powder X-ray diffractogram results of the crystalline modification type I compound prepared above were shown in FIG. 1 and a heat flow graph was shown in FIG. 2.

Example 2: Preparation of Crystalline Modification Type II Compound

Figure 3:
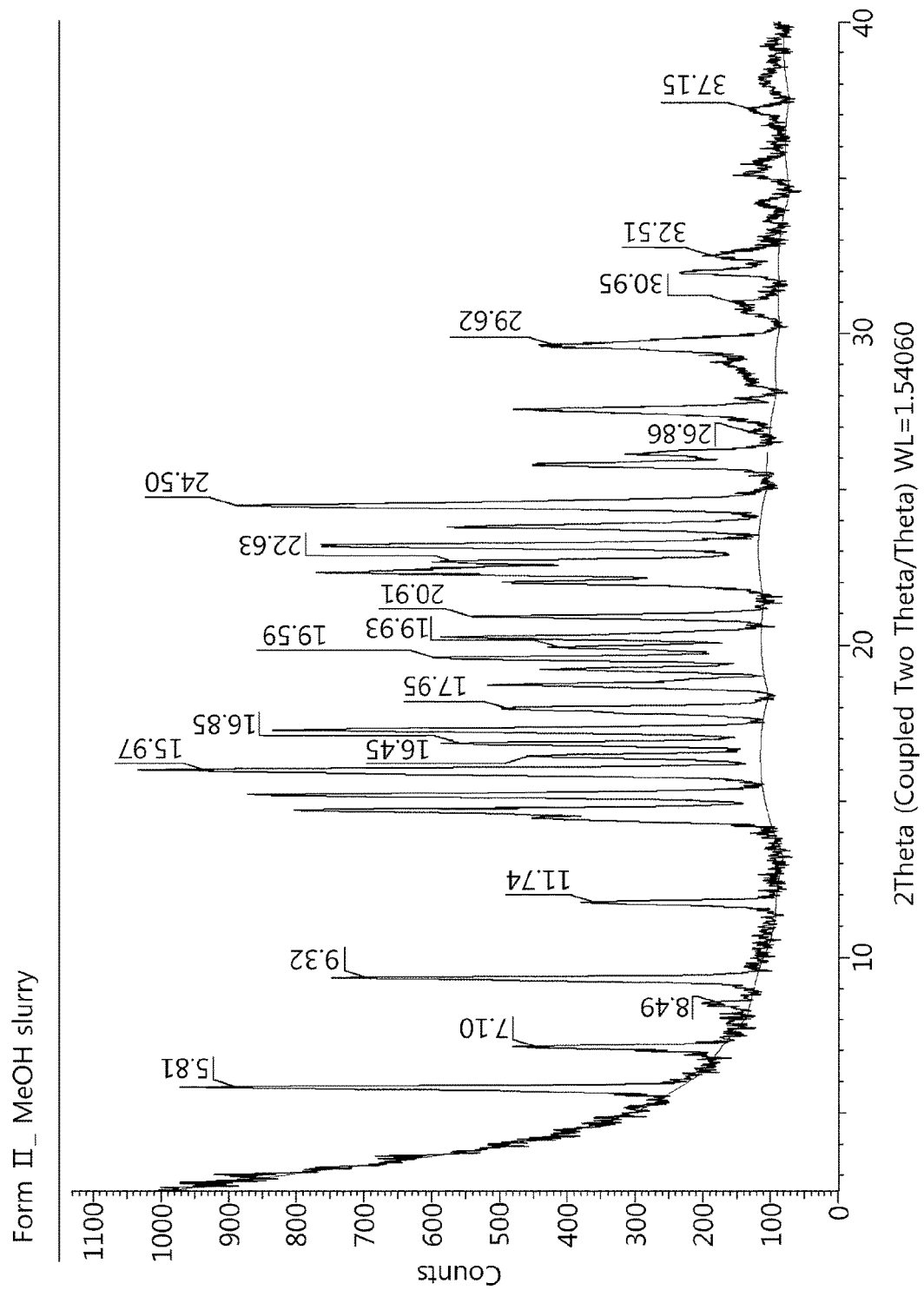
FIG. 3 shows a powder X-ray diffractogram of a crystalline modification type II compound of Chemical Formula 1 of the present disclosure.
Figure 4:
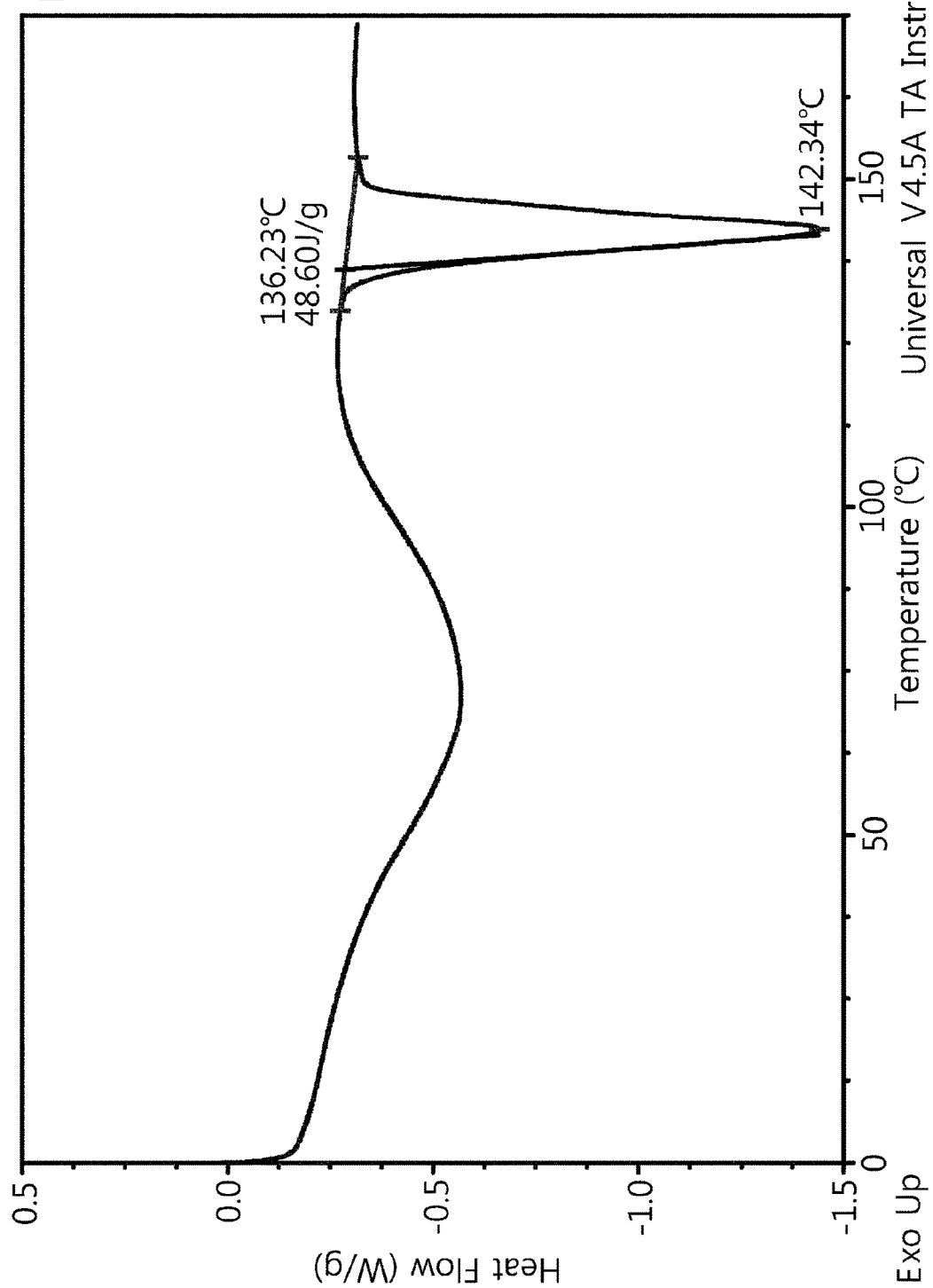
FIG. 4 shows a heat flow of the crystalline modification type II compound of Chemical Formula 1 of the present disclosure.

About 50 mg of the crystalline modification type I compound of Chemical Formula 1 was dispersed in 1 mL of methanol and shaken as slurry at room temperature for 24 hours at 100 rpm. The dispersion was then filtered, and the produced crystals were dried under reduced pressure at room temperature for 24 hours. Powder X-ray diffractogram results of the crystalline modification type II compound prepared above were shown in FIG. 3 and a heat flow graph was shown in FIG. 4.

Example 3: Preparation of Crystalline Modification Type III Compound

Figure 5:
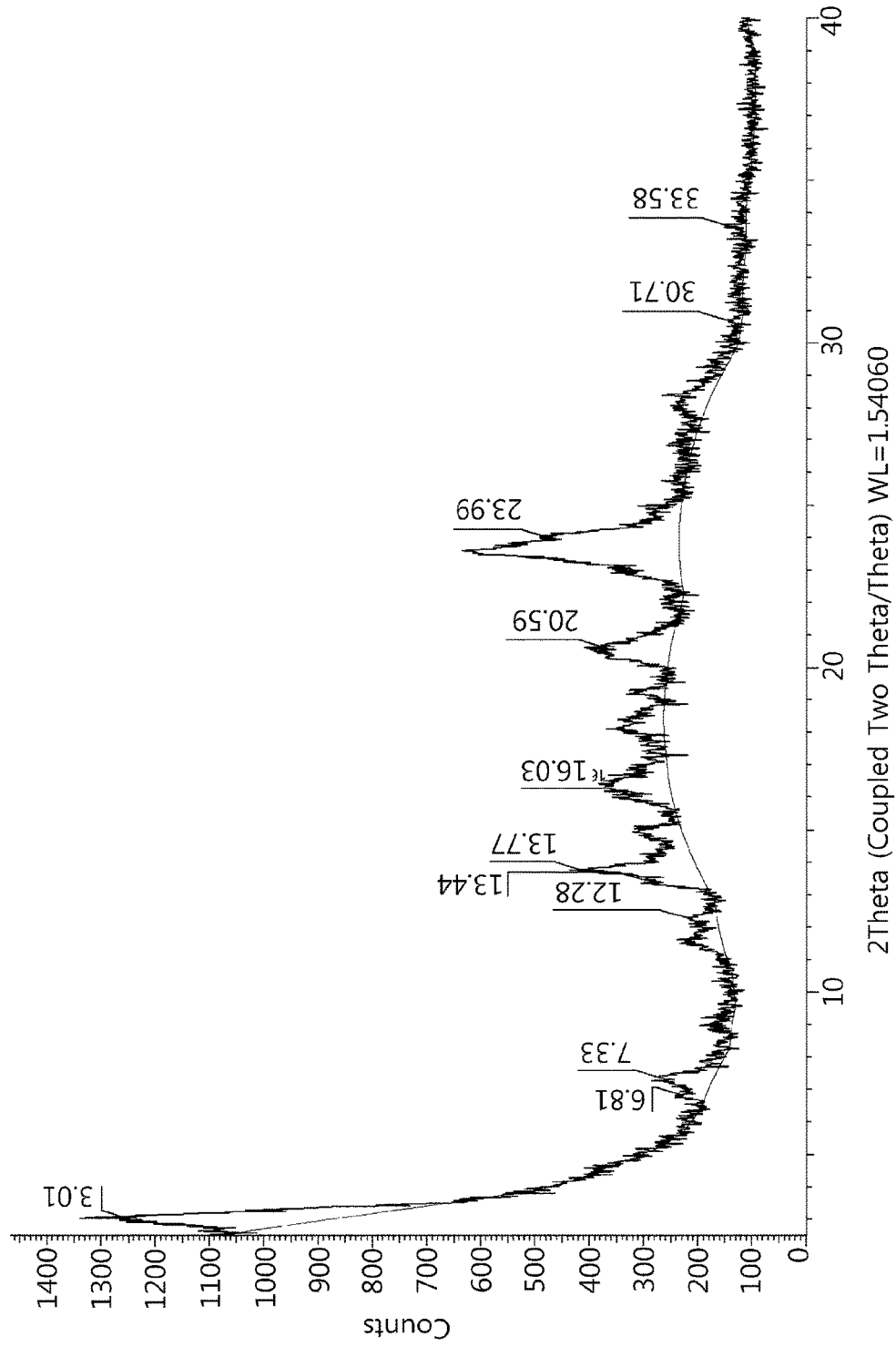
FIG. 5 shows a powder X-ray diffractogram of a crystalline modification type III compound of Chemical Formula 1 of the present disclosure.
Figure 6:
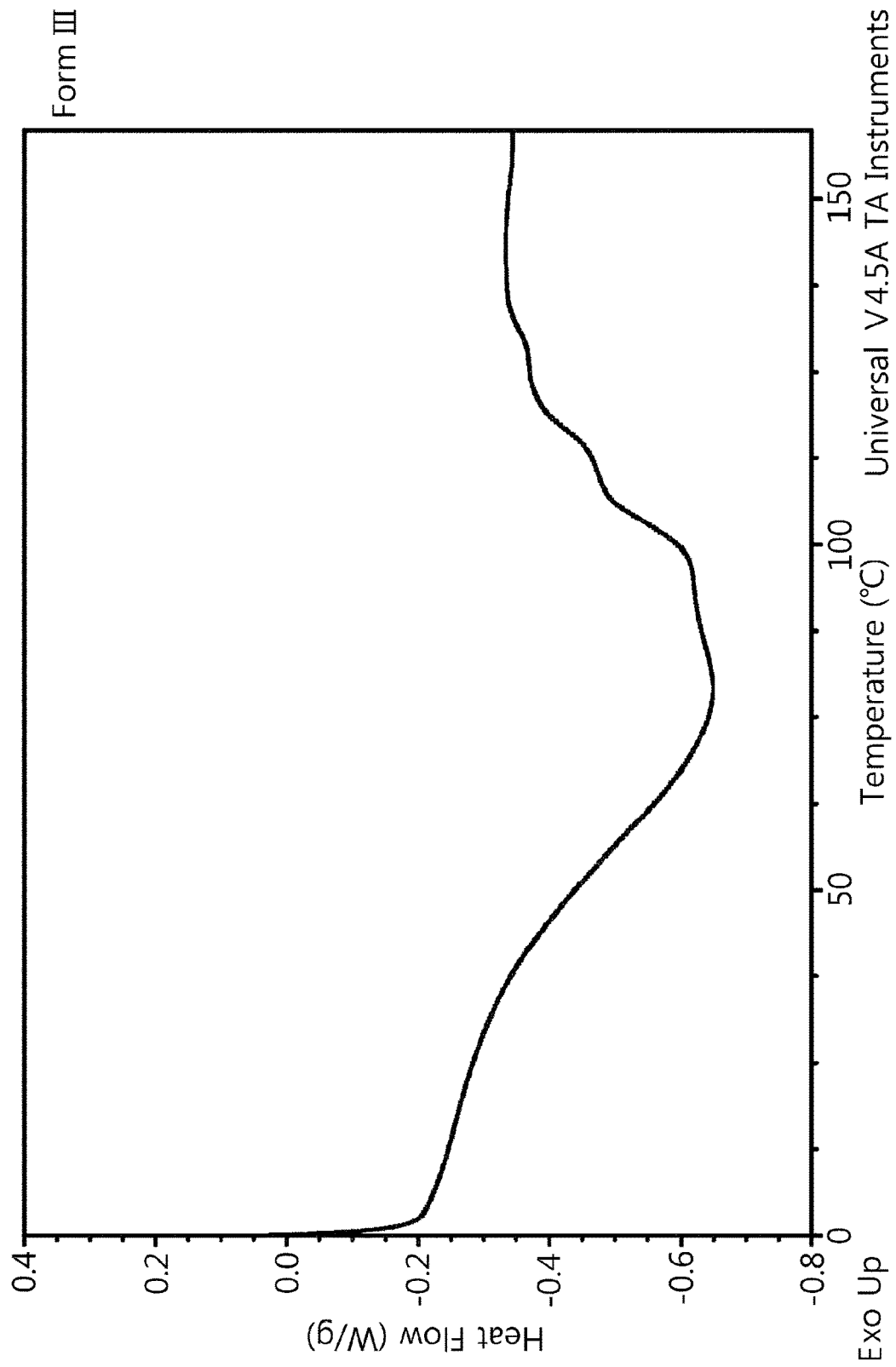
FIG. 6 shows a heat flow of the crystalline modification type III compound of Chemical Formula 1 of the present disclosure.

About 50 mg of the crystalline modification type I compound of Chemical Formula 1 was dissolved in 1 ml of tetrahydrofuran (THF). The prepared mixture was then filtered and the produced crystals were evaporated and dried at 40° C. Powder X-ray diffractogram results of the crystalline modification type III compound prepared above were shown in FIG. 5 and a heat flow graph was shown in FIG. 6.

Example 4: Preparation of Crystalline Modification Type IV Compound

Figure 7:
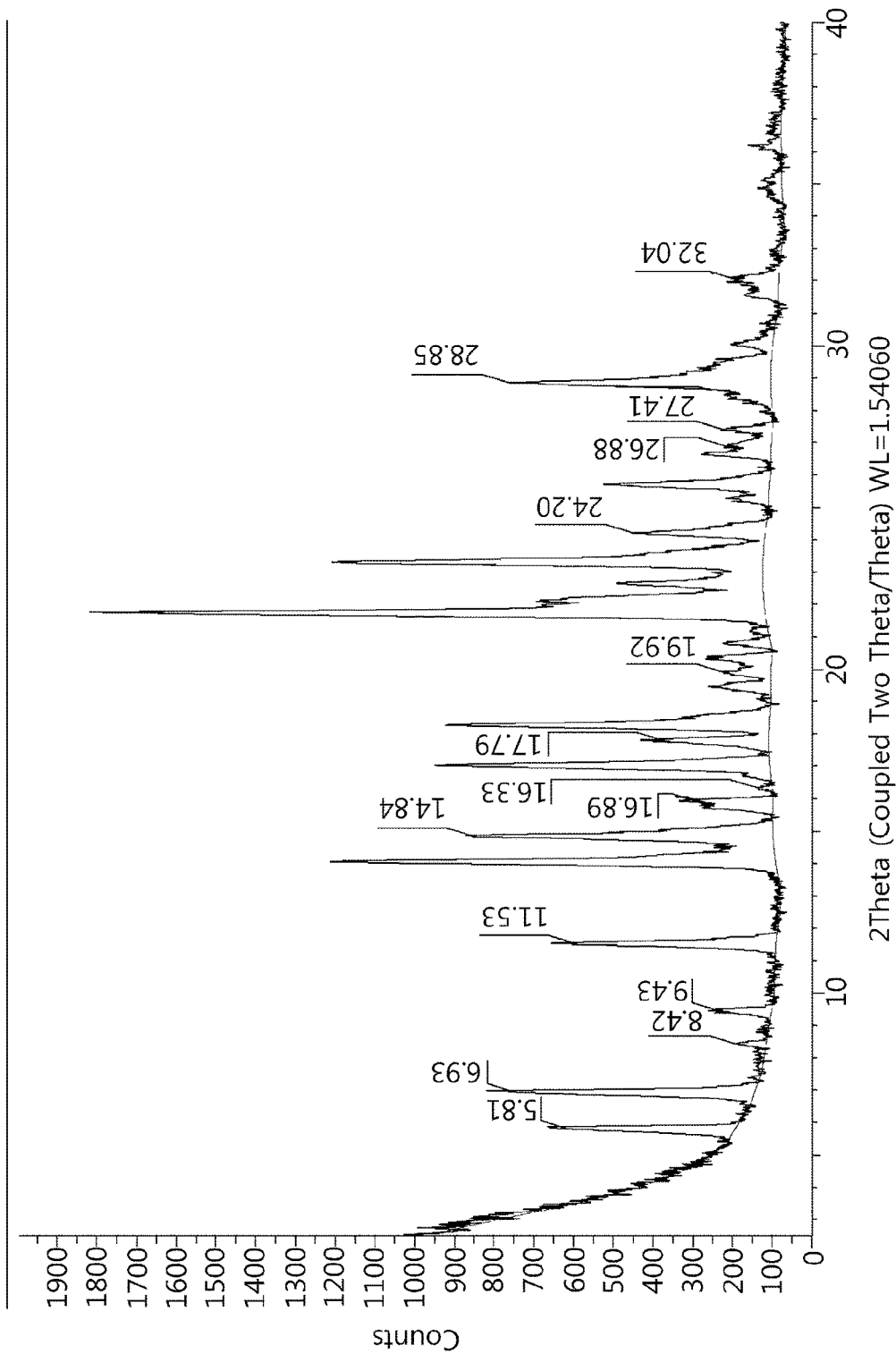
FIG. 7 shows a powder X-ray diffractogram of a crystalline modification type IV compound of Chemical Formula 1 of the present disclosure.
Figure 8:
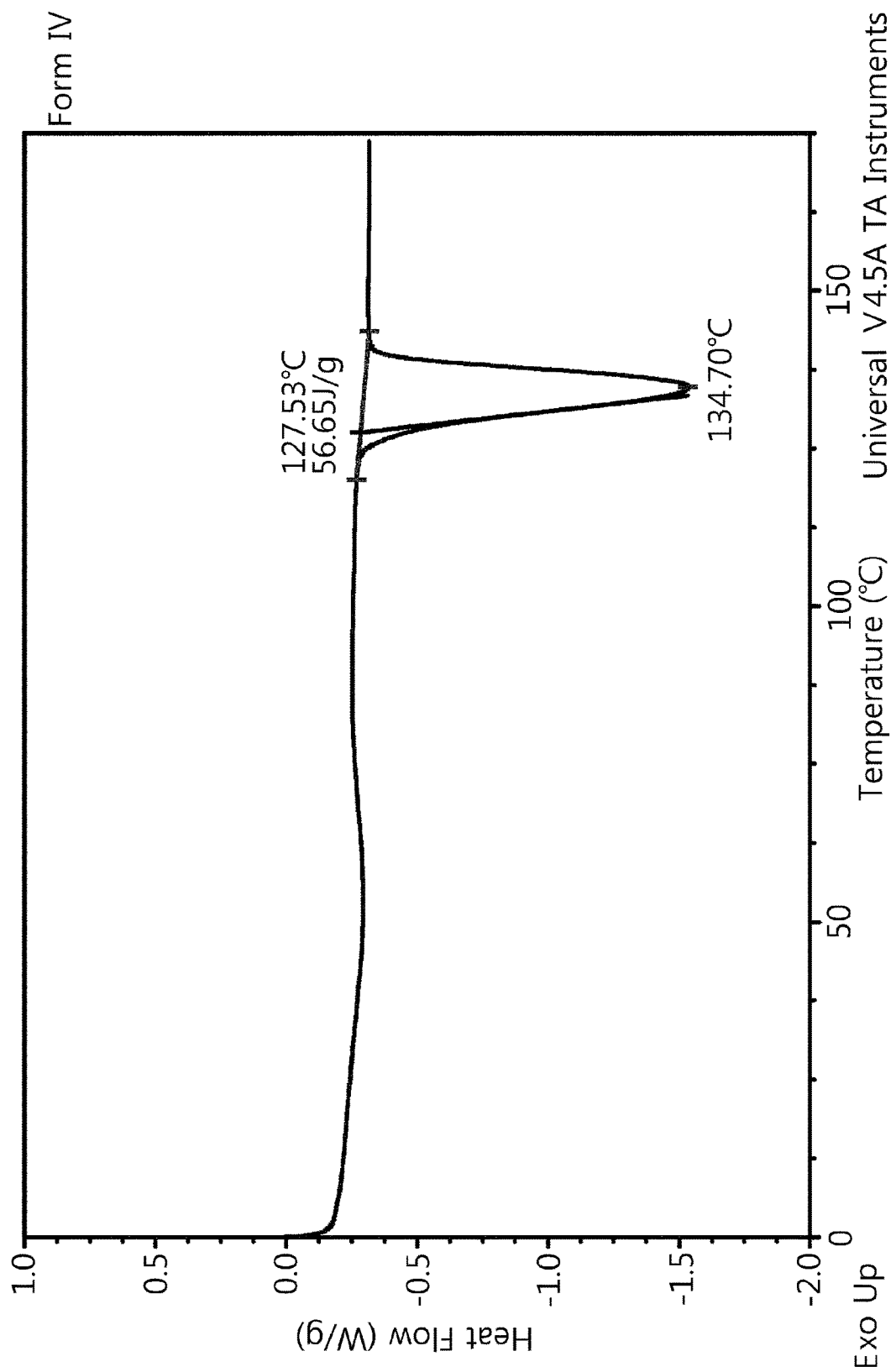
FIG. 8 shows a heat flow of the crystalline modification type IV compound of Chemical Formula 1 of the present disclosure.

About 50 mg of the crystalline modification type I compound of Chemical Formula 1 was dissolved in 0.5 ml of dichloromethane, and then added with 3 ml of acetonitrile, and the mixture was refrigerated for 4 hours. The crystals prepared above were filtered and dried at room temperature for 24 hours. Powder X-ray diffractogram results of the crystalline modification type IV compound prepared above were shown in FIG. 7 and a heat flow graph was shown in FIG. 8.

Example 5: Preparation of Crystalline Modification Type V Compound

Figure 9:
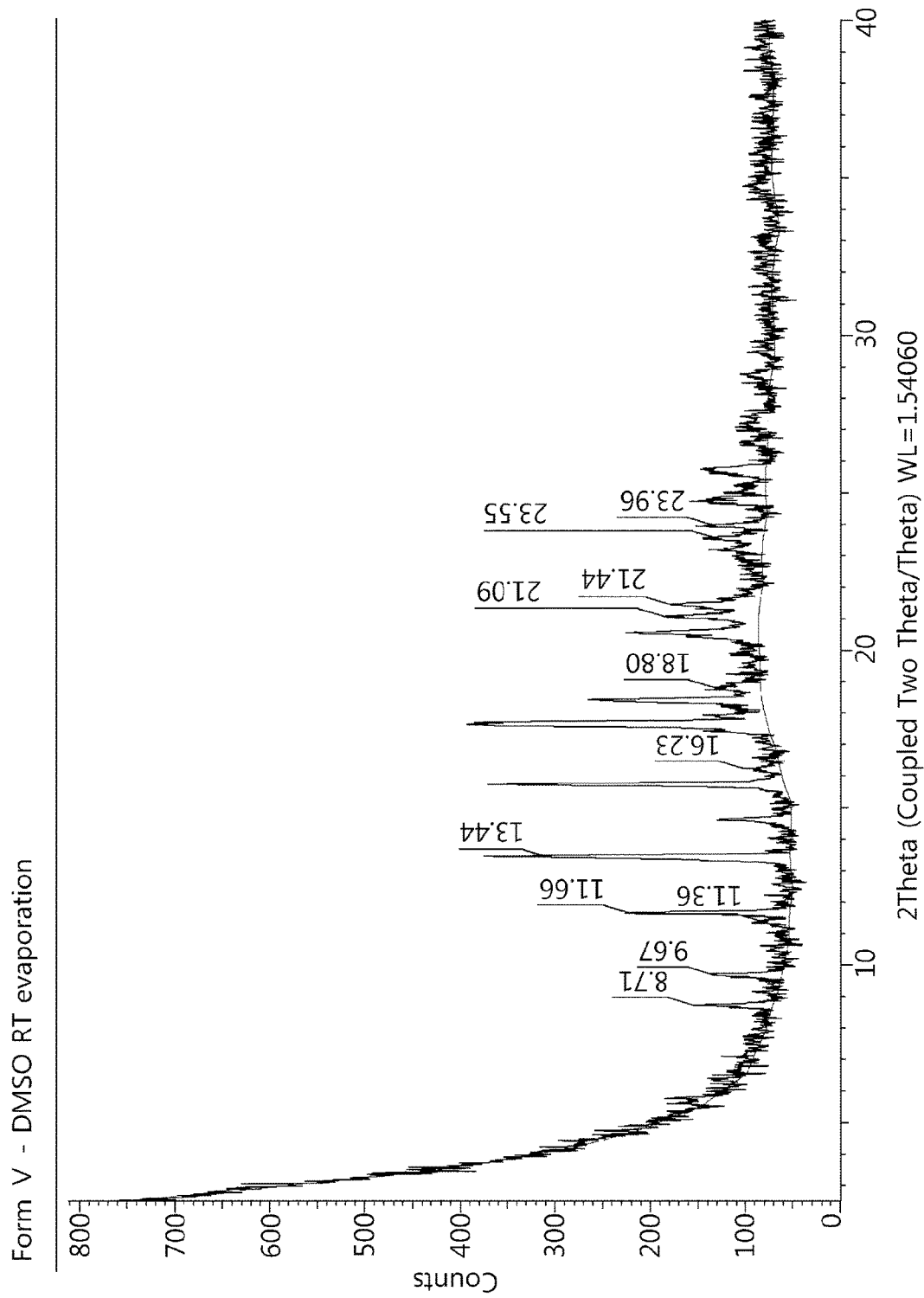
FIG. 9 shows a powder X-ray diffractogram of a crystalline modification type V compound of Chemical Formula 1 of the present disclosure.
Figure 10:
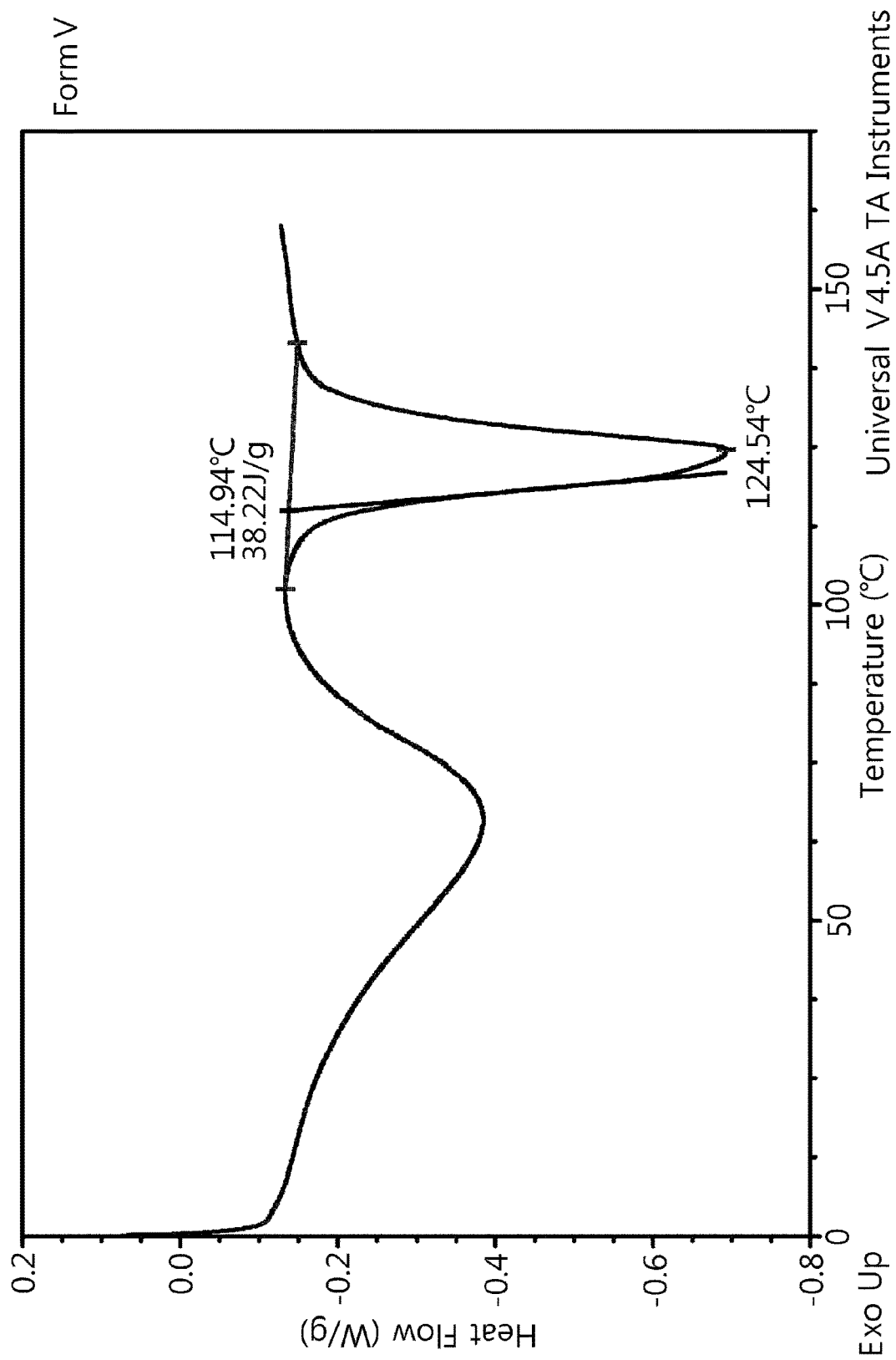
FIG. 10 shows a heat flow of the crystalline modification type V compound of Chemical Formula 1 of the present disclosure.

About 50 mg of the crystalline modification type I compound of Chemical Formula 1 was dissolved in 1 ml of dimethyl sulfoxide (DMSO). The prepared mixture was filtered, the solvent dimethylsulfoxide (DMSO) was completely evaporated, and the produced crystals were dried at room temperature for 24 hours. Powder X-ray diffractogram results of the crystalline modification type V compound prepared above were shown in FIG. 9 and a heat flow graph was shown in FIG. 10.

Example 6: Preparation of Crystalline Modification Type VI Compound

Figure 11:
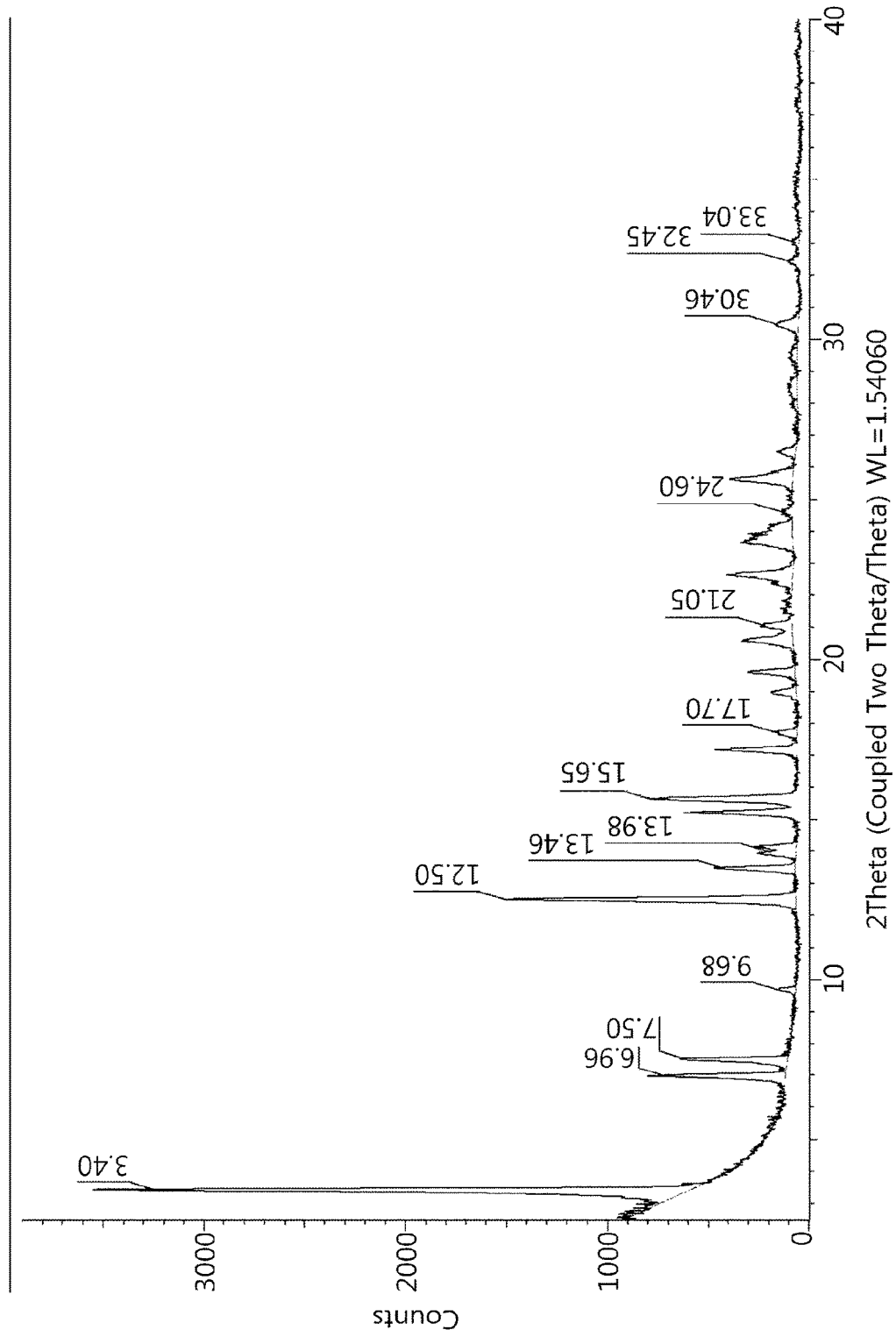
FIG. 11 shows a powder X-ray diffractogram of a crystalline modification type VI compound of Chemical Formula 1 of the present disclosure.
Figure 12:
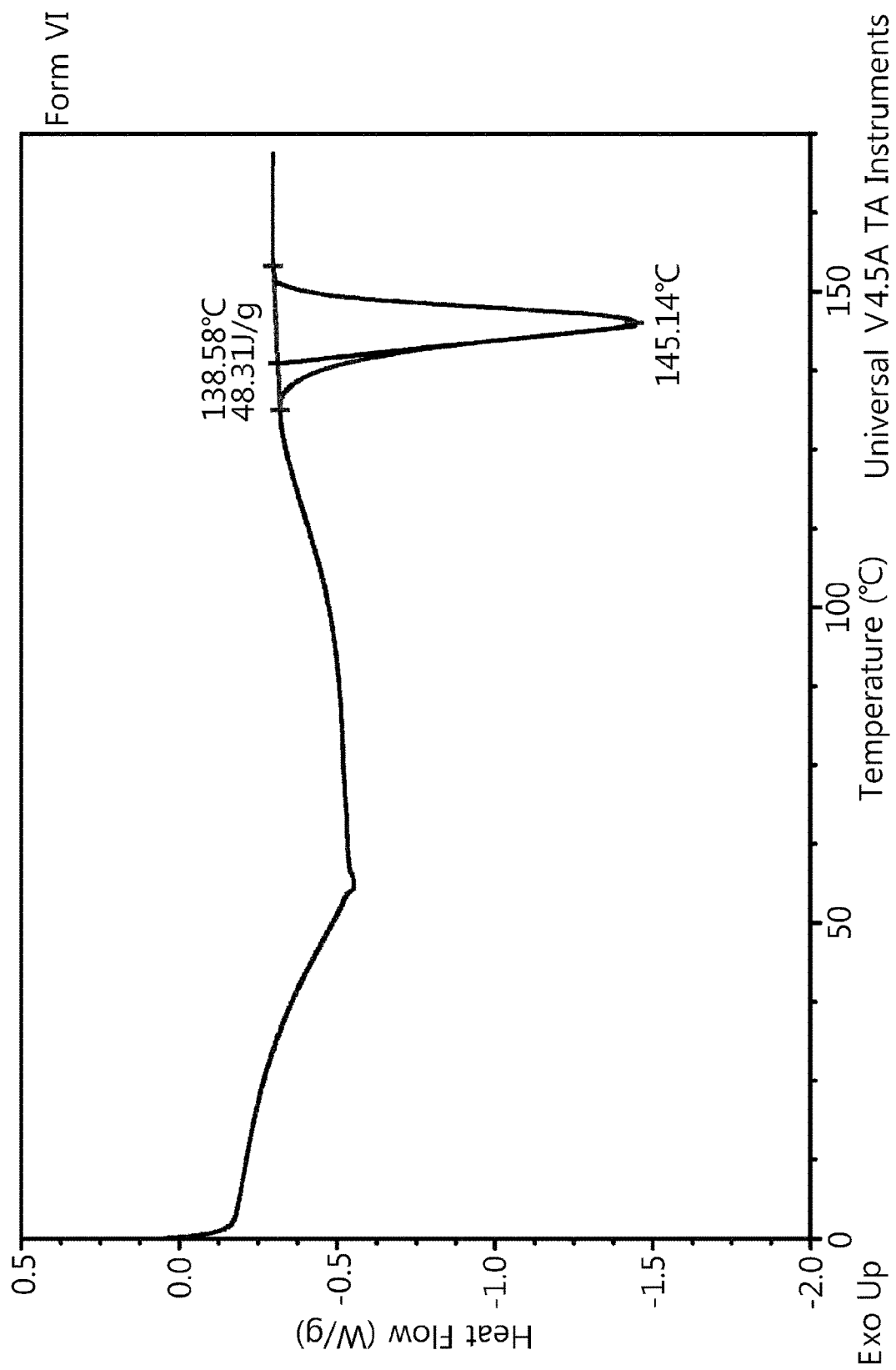
FIG. 12 shows a heat flow of the crystalline modification type VI compound of Chemical Formula 1 of the present disclosure.

About 50 mg of the crystalline modification type I compound of Chemical Formula 1 was dissolved in 0.5 ml of dichloromethane, filtered, and then added with 3 ml of methanol. The generated crystals were subsequently washed with distilled water and dried at room temperature for 24 hours. Powder X-ray diffractogram results of the crystalline modification type VI compound prepared above were shown in FIG. 11 and a heat flow graph was shown in FIG. 12.

Example 7: Preparation of Crystalline Modification Type VII Compound

Figure 13:
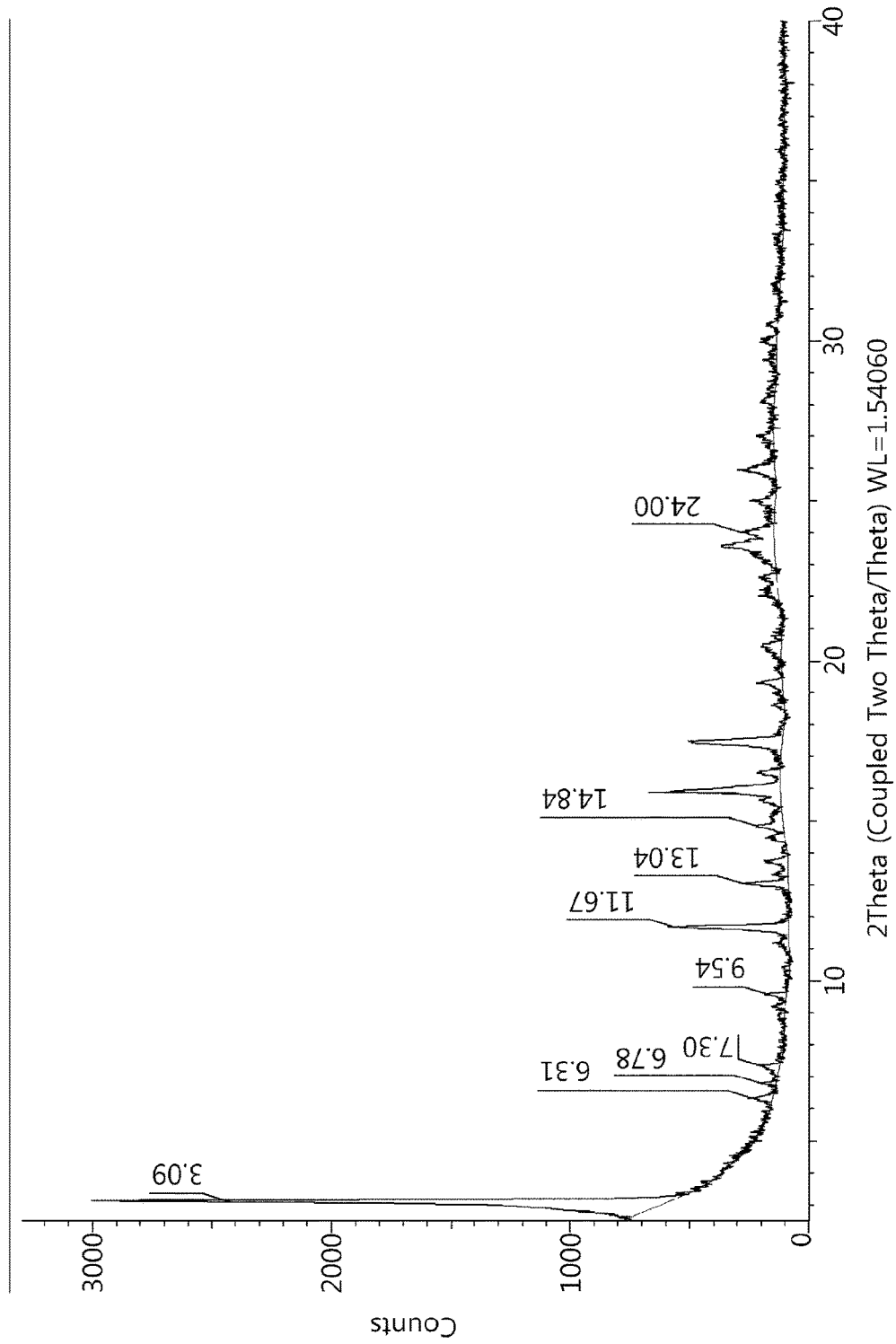
FIG. 13 shows a powder X-ray diffractogram of a crystalline modification type VII compound of Chemical Formula 1 of the present disclosure.
Figure 14:
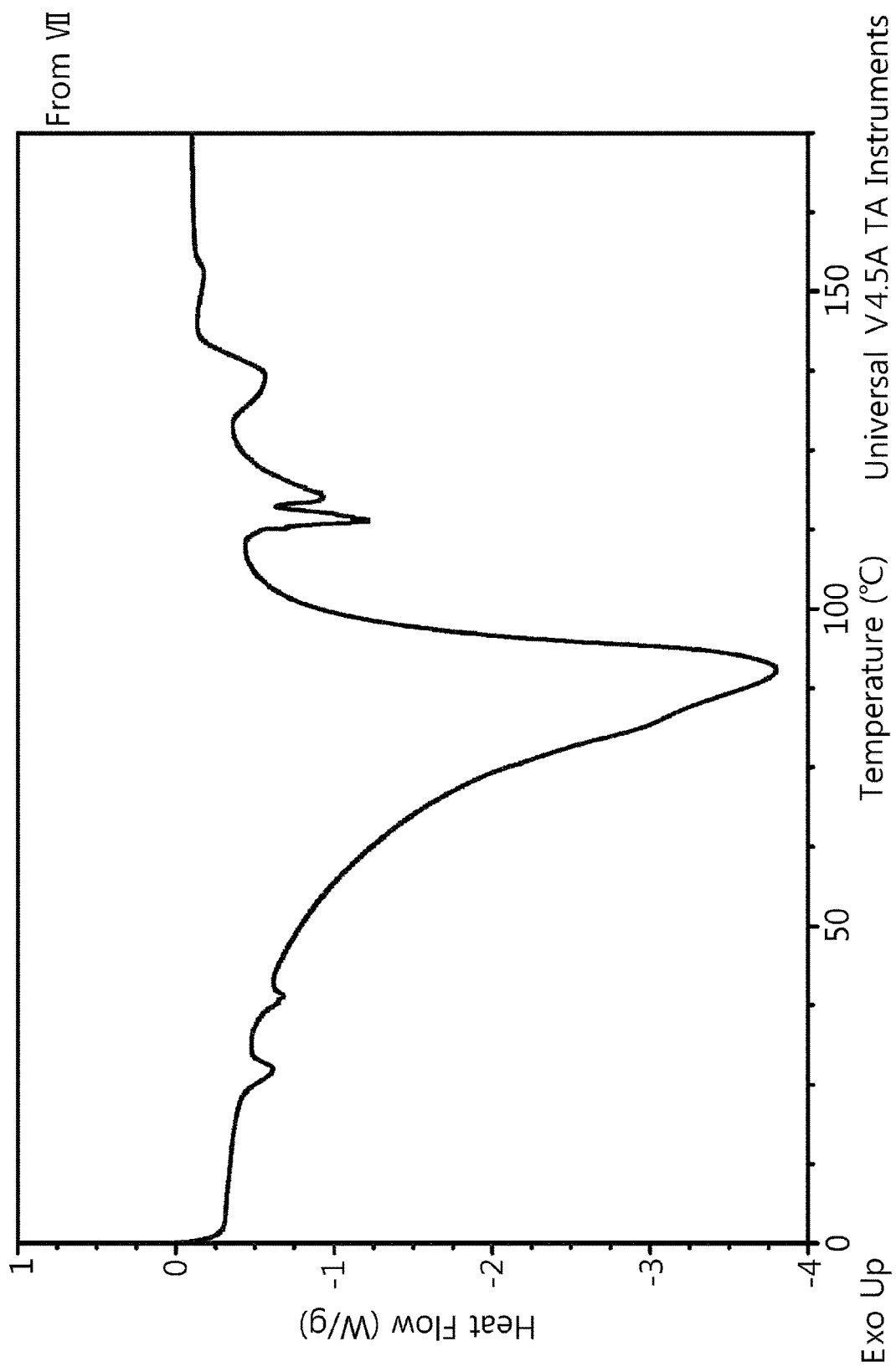
FIG. 14 shows a heat flow of the crystalline modification type VII compound of Chemical Formula 1 of the present disclosure.

About 50 mg of the crystalline modification type I compound of Chemical Formula 1 was dispersed in 1 mL of water and shaken as slurry at room temperature for 24 hours at 100 rpm. The dispersion was then filtered, and the produced crystals were dried at room temperature for 24 hours. Powder X-ray diffractogram results of the crystalline modification type VII compound prepared above were shown in FIG. 13 and a heat flow graph was shown in FIG. 14.

The invention claimed is:

1. A crystalline modification type I compound of the following Chemical Formula 1,

[Chemical Formula 1]

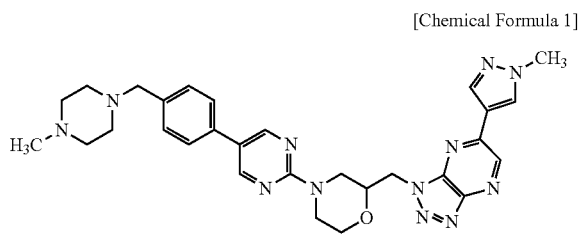

wherein angles of 2θ representing X-ray diffraction (XRD) peaks of the crystalline modification include 3.35°, 6.75°, 7.94°, 10.40° and 12.37° (°2θ, ±0.1° using Cu-Kα1 radiation).

2. The crystalline modification type I compound of claim 1, wherein the angles of 2θ representing XRD peaks further include 13.86°, 15.96°, 18.78°, and 19.89° (°2θ, ±0.1° using Cu-Kα1 radiation).

3. The crystalline modification type I compound of claim 2, wherein the angles of 2θ representing XRD peaks further include 20.59°, 21.01°, 24.82°, and 28.46° (°2θ, ±0.1° using Cu-Kα1 radiation).

4. A crystalline modification type II compound of the following Chemical Formula 1,

[Chemical Formula 1]

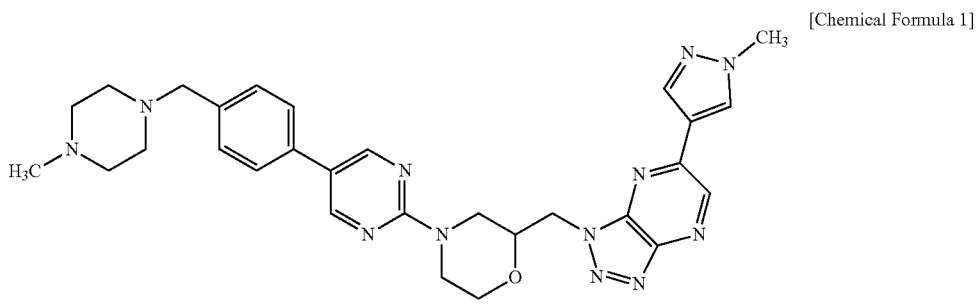

wherein angles of 2θ representing XRD peaks of the crystalline modification include 5.81°, 7.10°, 8.49°, 9.32°, 11.74°, 15.97°, and 16.45° (°2θ, ±0.1° using Cu-Kα1 radiation).

5. The crystalline modification type II compound of claim 4, wherein the angles of 2θ representing XRD peaks further include 16.85°, 17.95°, 19.59°, 19.93°, 20.91°, 22.63°, and 24.50° (°2θ, ±0.1° using Cu-Kα1 radiation).

6. The crystalline modification type II compound of claim 5, wherein the angles of 2θ representing XRD peaks further include 26.86°, 29.62°, 30.95°, 32.51°, and 37.15° (°2θ, ±0.1° using Cu-Kα1 radiation).

7. A crystalline modification type III compound of the following Chemical Formula 1,

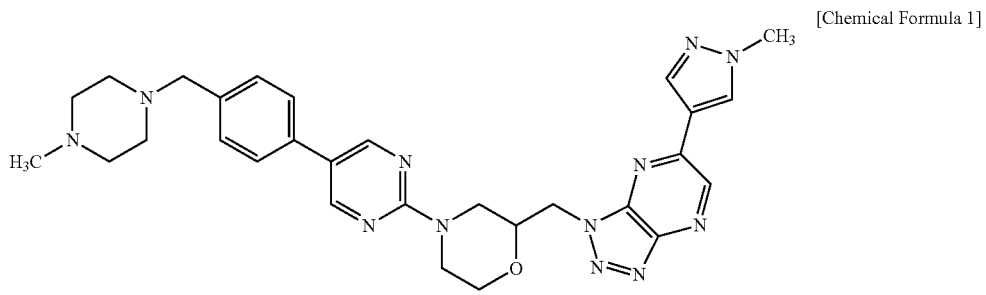

[Chemical Formula 1]

wherein angles of 2θ representing XRD peaks of the crystalline modification include 3.01°, 6.81°, 7.33°, and 12.28° (°2θ, ±0.1° using Cu-Kα1 radiation).

8. The crystalline modification type III compound of claim 7, wherein the angles of 2θ representing XRD peaks further include 13.44°, 13.77°, 16.03°, and 20.59° (°2θ, ±0.1° using Cu-Kα1 radiation).

9. The crystalline modification type III compound of claim 8, wherein the angles of 2θ representing XRD peaks further include 23.99°, 30.71°, and 33.58° (°2θ, ±0.1° using Cu-Kα1 radiation).

10. A crystalline modification type IV compound of the following Chemical Formula 1,

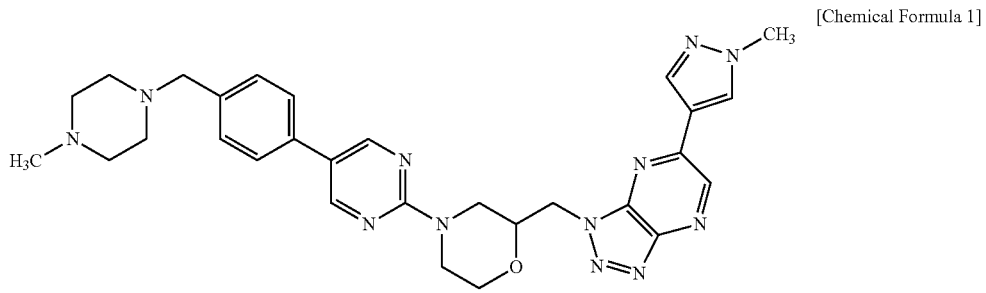

[Chemical Formula 1]

wherein angles of 2θ representing XRD peaks of the crystalline modification include 5.81°, 6.93°, 8.42°, 9.43°, and 11.53° (°2θ, ±0.1° using Cu-Kα1 radiation).

11. The crystalline modification type IV compound of claim 10, wherein the angles of 2θ representing XRD peaks further include 14.84°, 16.33°, 16.89°, 17.79°, and 19.92° (°2θ, ±0.1° using Cu-Kα1 radiation).

12. The crystalline modification type IV compound of claim 11, wherein the angles of 2θ representing XRD peaks further include 24.20°, 26.88°, 27.41°, 28.85°, and 32.04° (°2θ, ±0.1° using Cu-Kα1 radiation).

13. A crystalline modification type V compound of the following Chemical Formula 1,

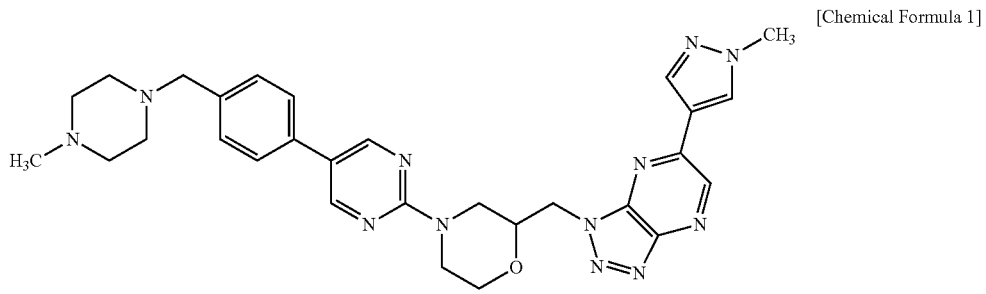

[Chemical Formula 1]

wherein angles of 2θ representing XRD peaks of the crystalline modification include 8.71°, 9.67°, 11.36°, and 11.66° (°2θ, ±0.1° using Cu-Kα1 radiation).

14. The crystalline modification type V compound of claim 13, wherein the angles of 2θ representing XRD peaks further include 13.44°, 16.23°, 18.80°, and 21.09° (°2θ, ±0.1° using Cu-Kα1 radiation).

15. The crystalline modification type V compound of claim 14, wherein the angles of 2θ representing XRD peaks further include 21.44°, 23.55°, and 23.96° (°2θ, ±0.1° using Cu-Kα1 radiation).

16. A crystalline modification type VI compound of the following Chemical Formula 1,

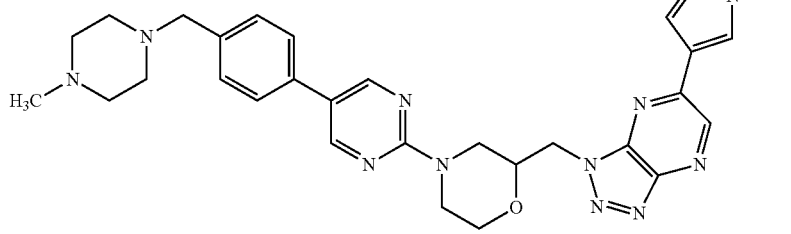
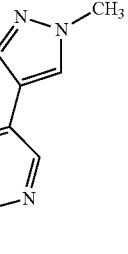

[Chemical Formula 1]

wherein angles of 2θ representing XRD peaks of the crystalline modification include 33.40°, 6.96°, 7.50°, 9.68°, and 12.50° (°2θ, ±0.1° using Cu-Kα1 radiation).

17. The crystalline modification type VI compound of claim 16, wherein the angles of 2θ representing XRD peaks further include 13.46°, 13.98°, 15.65°, 17.70°, and 21.05° (°2θ, ±0.1° using Cu-Kα1 radiation).

18. The crystalline modification type VI compound of claim 17, wherein the angles of 2θ representing XRD peaks further include 24.60°, 30.46°, 32.45°, and 33.04° (°2θ, ±0.1° using Cu-Kα1 radiation).

19. A crystalline modification type VII compound of the following Chemical Formula 1,

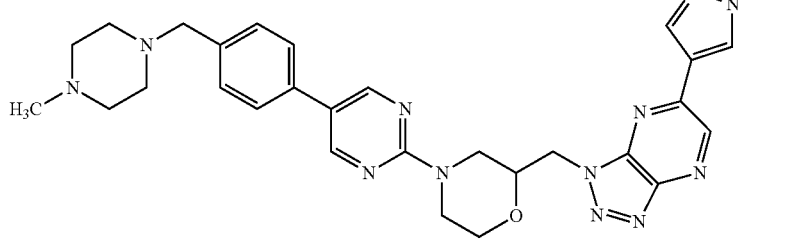

[Chemical Formula 1]

wherein angles of 2θ representing XRD peaks of the crystalline modification include 3.09°, 6.31°, and 6.78° (°2θ, ±0.1° using Cu-Kα1 radiation).

20. The crystalline modification type VII compound of claim 19, wherein the angles of 2θ representing XRD peaks further include 7.30°, 9.54°, and 11.67° (°2θ, ±0.1° using Cu-Kα1 radiation).

21. The crystalline modification type VII compound of claim 20, wherein the angles of 2θ representing XRD peaks further include 13.04°, 14.84°, and 24.00° (°2θ, ±0.1° using Cu-Kα1 radiation).

22. A pharmaceutical composition containing the crystalline modification of Chemical Formula 1 according to claim 1 as an active ingredient.

23. The pharmaceutical composition of claim 22, further comprising: at least one additional compound selected from pharmaceutically acceptable excipients, aids, adjuvants, diluents, and carriers.

24. A method of preparing the crystalline modification type I of claim 1, the method comprising:
(a) stirring 30 to 70 mg of the compound of Chemical Formula 1 in a solvent mixture consisting of 30 to 70 mL of ethanol (EtOH) and 1 to 3 mL of ethyl acetate (EA);
(b) stirring the dispersion produced in step (a) at 55 to 95° C. for 30 to 60 minutes and cooling the dispersion to 5 to 45° C. in an ice water bath; and
(c) recovering a material precipitated in step (b) by filtration, subsequently washing the precipitated material with distilled water, and drying the washed material under reduced pressure at 20 to 45° C.

25. A method of preparing the crystalline modification type II of claim 4, the method comprising:
(a) dissolving or dispersing 30 to 70 mg of a crystalline modification type I compound of Chemical Formula 1 in 0.5 to 2 mL of methanol;
(b) stirring the dispersion produced in step (a) at 15 to 28° C. for 1 to 24 hours; and
(c) recovering a material precipitated in step (b) by filtration, subsequently washing the precipitated material with distilled water, and drying the washed material under reduced pressure at 20 to 45° C. for 24 hours.

26. A method of preparing the crystalline modification type III of claim 7, the method comprising:
(a) dissolving 30 to 70 mg of a crystalline modification type I compound of Chemical Formula 1 in 0.5 to 2 mL of tetrahydrofuran (THF);

(b) stirring the dispersion produced in step (a) at 15 to 28° C. for 1 to 24 hours; and (c) recovering a material precipitated in step (b) by filtration, subsequently washing the precipitated material with distilled water, and evaporating and drying the washed material under reduced pressure at 20 to 60° C. for 24 hours.

27. A method of preparing the crystalline modification type IV of claim 10, the method comprising:
   (a) dissolving or dispersing 30 to 70 mg of a crystalline modification type I compound of Chemical Formula 1 in 0.5 to 1 mL of dichloromethane;
   (b) stirring the dispersion produced in step (a) at 15 to 28° C. for 1 to 24 hours;
   (c) adding 1 to 5 mL of acetonitrile (ACN) to the solution of step (b) and refrigerating the mixture for 4 hours; and
   (d) filtering the compound produced in step (c) and then drying the filtered compound at 15 to 28° C. for 24 hours.

28. A method of preparing the crystalline modification type V of claim 13, the method comprising:
   (a) dissolving 30 to 70 mg of a crystalline modification type I compound of Chemical Formula 1 in 0.5 to 1 mL of dimethylsulfoxide (DMSO);
   (b) stirring the dispersion produced in step (a) at 15 to 28° C. for 1 to 24 hours; and
   (c) filtering a material precipitated in step (b), completely evaporating the solvent dimethylsulfoxide (DMSO), and then drying the evaporated mixture.

29. A method of preparing the crystalline modification type VI of claim 16, the method comprising:
   (a) dissolving or dispersing 30 to 70 mg of a crystalline modification type I compound of Chemical Formula 1 in 0.2 to 1 mL of dichloromethane;
   (b) stirring the dispersion produced in step (a) at 15 to 28° C. for 1 to 24 hours; and
   (c) recovering a material precipitated in step (b) by filtration, adding 1 to 4 mL of methanol, and then subsequently washing the produced crystals with distilled water, and drying the produced crystals at 15 to 28° C.

30. A method of preparing the crystalline modification type VII of claim 19, the method comprising:
   (a) dissolving or dispersing 30 to 70 mg of a crystalline modification type I compound of Chemical Formula 1 in 0.5 to 2 mL of water;
   (b) stirring a dispersion produced in step (a) at 15 to 28° C. for 1 to 24 hours; and
   (c) recovering a material precipitated in step (b) by filtration and drying the recovered material at 15 to 28° C.

* * * * *